United States Patent
Kitagawa et al.

(10) Patent No.: US 6,329,031 B1
(45) Date of Patent: Dec. 11, 2001

(54) POLYESTER RESIN COMPOSITION AND REDUCED PRESSURE BLOOD-COLLECTING TUBE

(75) Inventors: Hironobu Kitagawa; Mitsuhiro Harada; Hirotoshi Sonoda; Yoshitaka Eto, all of Otsu (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/261,306

(22) Filed: Mar. 2, 1999

(51) Int. Cl.$^7$ .................... A61B 19/00; B29D 23/00; C08G 63/668

(52) U.S. Cl. ............... 428/35.7; 428/35.6; 428/36.9; 604/403; 604/415

(58) Field of Search ................. 428/35.7, 36.6, 428/36.9; 604/403, 415

(56) References Cited

U.S. PATENT DOCUMENTS 4,643,925 * 2/1987 Smith et al. ................ 428/35
4,985,026 * 1/1991 Kasai et al. ................ 604/403
5,213,856 * 5/1993 Poó et al. ................ 428/34.1

FOREIGN PATENT DOCUMENTS 10-130480   6/1998   (JP) .

\* cited by examiner

Primary Examiner—Harold Pyon
Assistant Examiner—Sandra M. Nolan
(74) Attorney, Agent, or Firm—Kenyon & Kenyon

(57) ABSTRACT

The present invention provides a polyester resin composition comprising (A) 10 to 90% by weight of a polyethylene terephthalate polymer having 100 to 75 mole % of ethylene terephthalate units and (B) 90 to 10% by weight of a polyester resin wherein the polyester resin composition when molded into a sheet has an oxygen permeability coefficient of 3.0 or less cc-mm/m$^2$day·atm. The polyester resin composition of the present invention gives a molded product which is outstanding in transparency, gas barrier property, ultraviolet-screening property and impact strength and therefore suitable as a reduced pressure blood-collecting tube.

11 Claims, No Drawings

POLYESTER RESIN COMPOSITION AND REDUCED PRESSURE BLOOD-COLLECTING TUBE

FIELD OF THE INVENTION

The present invention relates to a novel polyester resin composition which can form a molded product excellent in transparency, gas barrier property, ultraviolet-screening property, impact strength and the like, and to a reduced pressure blood-collecting tube made using said molded product.

BACKGROUND OF THE INVENTION

Polyethylene terephthalate polymers (which may be hereinafter referred to as "PET") having ethylene terephthalate units as major structural units have been heretofore widely used for forming molded products such as packaging materials, containers and the like because of their superior properties such as high mechanical strength, transparency, gas barrier property, and hygienic qualities.

However, such PET packaging materials and containers are not always sufficient in gas barrier property against oxygen or other gases, and are unsatisfactory for the drawback of changing the properties of contents in the case of long-term storage, small-size containers or requirement for high gas barrier property. Packaging materials and containers should be essentially transparent to permit inspection of contents and, in such case, should protect the contents against the degradation and the discoloration thereof which occur due to ultraviolet ray irradiation.

For improvements in the gas barrier property of PET packaging materials and containers, it has been proposed to laminate an ethylene-vinyl alcohol copolymer, polyamide resin or other resins which are superior to PET in gas barrier property. However, when a multi-layer structure on PET is stretched, interlaminar separation may occur for a low adhesion of the resins to PET, presumably leading to impairment of gas barrier property. Further because of their low compatibility with PET, these resins of the defective multi-layer molded product can not be reused by mixing with a virgin material to produce a transparent molded product.

A mixture of PET and polyethylene isophthalate or a copolymer thereof was proposed (Japanese Unexamined Patent Publications Nos. 64,624/1984; 64,658/1984; and 315,457/1989). However, a molded product made of the proposed mixture is low in gas barrier property and heat resistance.

A glass tube with a bottom end has been used as a container of high gas barrier property, especially as a reduced pressure blood-collecting tube because it is capable of retaining the reduced pressure for a prolonged time. Yet, since such glass tube is readily damaged and is difficult to handle for its weight, it is currently being replaced by a plastic tube. Nevertheless the plastic reduced pressure blood-collecting tube poses the following problem. The plastic tube has a low gas barrier property compared with the glass tube so that the level of reduced pressure in the tube is decreased with time, and the amount of collected blood is diminished accordingly. For this reason, when a reduced pressure blood-collecting tube is produced, it is necessary to use a resin composition capable of forming a molded product of high gas barrier property.

PET, polyethylene, polypropylene or the like is used as a plastic constituting a reduced pressure blood-collecting bottom-ended tube. Among them, polyethylene is low in transparency and gas barrier property, and is not satisfactory as a plastic constituting a reduced pressure blood-collecting tube. Polypropylene is superior in transparency but inferior in gas barrier property like polyethylene, and is unsatisfactory as a plastic constituting a reduced pressure blood-collecting bottom-ended tube. PET is outstanding in moldability and transparency but low in gas barrier property. Various improvements have been made in the plastics constituting a reduced pressure blood-collecting bottom-ended tube.

For example, Japanese Unexamined Patent Publication No.45,040/1990 proposed a reduced pressure blood-collecting bottom-ended tube made from a mixture of PET and a copolymer of polyethylene isophthalate. However, the proposed tube is defective in the following. 1,3-bis(2-hydroxyethoxy)benzene used as one of the monomers for the copolymer is expensive and is responsible for a high cost of the obtained copolymer. Furthermore, because the copolymer has low impact resistance, the resulting tube is inferior in impact strength, especially drop impact strength. Japanese Unexamined Patent Publication No.22,294/1995 proposed a vacuum blood-collecting tube formed from a mixture of PET with polyester of isophthalic acid, terephthalic acid, 1,3-bis(2-hydroxyethoxy)benzene and ethylene glycol. The proposed tube, however, calls for use of expensive material and is poor in drop impact strength as is the case with the proposal of Japanese Unexamined Patent Publication No.45,040/1990. Hence it is unsatisfactory.

SUMMARY OF THE INVENTION

An object of the present invention is to provide a polyester resin composition which is free of the foregoing drawbacks or problems of conventional techniques, the composition being useful in producing a molded product excellent in transparency, gas barrier property, ultraviolet-screening property, and impact strength.

Another object of the invention is to provide a reduced pressure blood-collecting bottom-ended tube which shows substantially no change in the amount of collected blood with time for a high gas barrier property, the tube being excellent in ultraviolet-screening property, transparency and impact strength, especially drop impact strength.

Other objects and features of the present invention will become more apparent from the following description.

According to the present invention, there is provided a polyester resin composition comprising:

(A) 10 to 90% by weight of a polyethylene terephthalate polymer having 100 to 75 mole % of ethylene terephthalate units; and (B) 90 to 10% by weight of a polyester resin, the polyester resin being prepared by polycondensation of dicarboxylic acid component and glycol component, the dicarboxylic acid component comprising, based on the total amount of the dicarboxylic acid component, 50 to 92 mole % of isophthalic acid or its ester-forming derivative, 5 to 47 mole % of terephthalic acid or its ester-forming derivative and 3 to 45 mole % of 2,6-naphthalenedicarboxylic acid or its ester-forming derivative, and the glycol component comprising, based on the total amount of the glycol component, 75 to 96.5 mole % of ethylene glycol and 3.5 to 25 mole % of diethylene glycol, the polyester resin composition having an oxygen permeability coefficient of 3.0 or less cc·mm/m$^2$·day·atm.

The present invention is also directed to a molded product formed from said polyester resin composition, and to a reduced pressure blood-collecting tube having a bottom at one end thereof and a plug for closing the opening at the other end thereof, said tube being molded from said polyester resin composition.

The present inventors conducted extensive research to achieve the foregoing objects and found that when said specific polyester resin composition is used, a molded product is produced which is excellent in gas barrier property, impact strength, especially drop impact strength, transparency, and ultraviolet-screening property, and that the reduced pressure blood-collecting tube made using the molded product of the polyester resin composition shows little variations with time in the amount of collected blood and is superior in ultraviolet-screening property, drop impact strength, transparency and the like. The present invention was completed based on these novel findings.

DETAILED DESCRIPTION

The polyester resin composition of the present invention comprises the polyethylene terephthalate polymer (A) and the polyester resin (B).

The polyethylene terephthalate polymer (A) in the polyester resin composition of the invention is a thermoplastic polyester resin containing 100 to 75 mole %, preferably 100 to 80 mole %, more preferably 100 to 85 mole %, of ethylene terephthalate units.

When the polyethylene terephthalate polymer (A) contains other units than the ethylene terephthalate units, dicarboxylic acid component as polycondensation component in the polymer (A) include, in addition to terephthalic acid or its ester-forming derivative, isophthalic acid, 2,6-naphthalenedicarboxylic acid, 2,7-naphthalenedicarboxylic acid, diphenoxyethane-dicarboxylic acid, 4,4'-biphenyldicarboxylic acid and other aromatic dicarboxylic acids or their ester-forming derivatives, succinic acid, adipic acid, sebacic acid, azelaic acid and other aliphatic dicarboxylic acids or their ester-forming derivatives, cyclohexanedicarboxylic acid, hexahydroterephthalic acid, hexahydroisophthalic acid and other alicyclic dicarboxylic acids or their ester-forming derivatives, p-hydroxybenzoic acid, hydroxycaproic acid and other hydroxy acids or their ester-forming derivatives, and the like. Among them, preferred dicarboxylic acid component are isophthalic acid and hexahydroterephthalic acid as well as terephthalic acid.

When the polyethylene terephthalate polymer (A) contains other units than the ethylene terephthalate units, glycol component as polycondensation component in the polymer (A) include not only ethylene glycol but propylene glycol, trimethylene glycol, tetramethylene glycol, pentamethylene glycol, hexamethylene glycol, neopentyl glycol, diethylene glycol and other aliphatic glycols, 1,4-cyclohexanedimethanol and other alicyclic glycols, bisphenol A, alkylene oxide adduct of bisphenol A and other aromatic glycols, polyethylene glycol, polypropylene glycol, polytetramethylene glycol and other polyglycols, and the like. Among them, preferred glycols are 1,4-cyclohexanedimethanol, 1,3-propylene glycol and tetramethylene glycol as well as ethylene glycol.

When the polyethylene terephthalate polymer (A) contains other units than the ethylene terephthalate units, polyfunctional compound component as the polycondensation component in the polymer (A) may be included. Acid component useful as the polycondensation component include, for example, trimellitic acid, pyromellitic acid and the like. Glycol component useful as the polyfunctional compound component include, for example, glycerin, pentaerythritol and the like. The amount of the polyfunctional compound component to be used should be limited to the range wherein the polyethylene terephthalate polymer (A) can substantially retain the linear form.

The polyethylene terephthalate polymer (A) can be prepared by conventional methods such as a direct esterification method and an ester exchange method. The direct esterification method comprises directly reacting terephthalic acid with ethylene glycol and, when required, other polycondensation component for esterification and distilling off water from the reaction mixture, followed by polycondesation under reduced pressure. The ester exchange method comprises reacting dimethyl terephthalate or like ester-forming derivative with ethylene glycol and, when required, other polycondensation component for ester-exchange, distilling off methyl alcohol from the reaction mixture, and subjecting the mixture to polycondensation under reduced pressure. Optionally, solid-phase polymerization may be carried out to increase the intrinsic viscosity of the resin and to reduce the acetaldehyde content.

The polyethylene terephthalate polymer (A) usually has an intrinsic viscosity (IV) of 0.4 to 1.2 dl/g, preferably 0.50 to 1.0 dl/g, more preferably 0.52 to 0.90 dl/g.

In the ester exchange reaction or esterification reaction and polycondensation reaction, it is preferred to use a reaction catalyst and a reaction stabilizer.

Useful catalysts for the ester exchange reaction are magnesium compounds, manganese compounds, calcium compounds, zinc compounds and the like, and include their acetates, monocarboxylates, alcoholates and oxides. While the esterification reaction can be performed using terephthalic acid, ethylene glycol and optionally other polycondensation component without using a catalyst, the reaction is also feasible in the presence of a polycondensation catalyst.

Useful polycondensation catalysts are germanium compounds, titanium compounds, antimony compounds and the like and include, for example, germanium dioxide, germanium hydroxide, germanium alcoholate, titanium tetrabutoxide, titanium tetraisopropoxide, titanium oxalate, antimony trioxide and the like.

Phosphorus compounds are preferably used as the reaction stabilizer. Preferred phosphorus compounds include, for example, phosphoric acid, esters thereof, phosphorous acid, esters thereof, hypophosphorous acid, esters thereof and the like.

To prevent the production of diethylene glycol as a by-product in the esterification reaction, it is possible to use triethyl amine and other tertiary amines, tetraethylammonium hydroxide and other quaternary ammonium hydroxides, sodium carbonate and other basic compounds, and the like.

The polyethylene terephthalate polymer (A) may contain heat stabilizers, thermal-oxidative stabilizers, antistatic agents, weathering stabilizers, lubricants, dyes, pigments, dispersants, and the like within the range not adversely affecting the objects of the present invention.

The polyester resin (B) in the composition of the invention is a thermoplastic polyester resin prepared by polycondensation of dicarboxylic acid component and glycol component, the dicarboxylic acid component comprising, based on the total amount of the dicarboxylic acid component, 50 to 92 mole % of isophthalic acid or its ester-forming derivative, 5 to 47 mole % of terephthalic acid or its ester-forming derivative and 3 to 45 mole % of 2,6-naphthalene-dicarboxylic acid or its ester-forming derivative, and the glycol component comprising, based on the total amount of the glycol component, 75 to 96.5 mole % of ethylene glycol and 3.5 to 25 mole % of diethylene glycol.

A sheet formed from the polyester resin preferably has an oxygen permeability coefficient of 3.0 or less cc·mm/m$^2$·day·atm, especially 1.8 or less cc·mm/m$^2$·day·atm, so that the composition of the invention has an oxygen permeability coefficient of 3.0 or less cc·mm/m$^2$·day·atm.

In preparing the polyester resin (B), a specific amount of diethylene glycol is used as the glycol component, whereby the molded product is significantly improved in impact strength, especially drop impact strength without reduction in gas barrier property of the molded product.

When the amount of isophthalic acid or its ester-forming derivative in the dicarboxylic acid component is less than 50 mole %, the molded product is impaired in gas barrier property. When the amount of terephthalic acid or its ester-forming derivative in the dicarboxylic acid component is less than 5 mole %, the molded product is rendered opaque because of its low compatibility with the polyethylene terephthalate polymer (A). When the amount of 2,6-naphthalenedicarboxylic acid or its ester-forming derivative in the dicarboxylic acid component is less than 3 mole %, the molded product is lowered in ultraviolet-screening property. Hence, it is undesirable to use the dicarboxylic acid component in amounts outside said ranges.

When the amount of diethylene glycol in the glycol component is less than 3.5 mole %, the molded product is reduced in drop impact strength, whereas the amount of more than 25 mole % lowers the heat resistance of the molded product. Hence both cases are undesirable.

The amount of diethylene glycol in the glycol component is a combined amount of diethylene glycol used as the raw material and diethylene glycol given in a small amount by dimerization of ethylene glycol in the polycondensation. The amount of diethylene glycol can be determined by the analysis of the obtained polyester resin through, e.g. $^1$H-NMR.

The dicarboxylic acid component of the polyester resin contain, based on total amount of the dicarboxylic acid component, preferably 70 to 90 mole %, more preferably 72 to 90 mole %, of isophthalic acid or its ester-forming derivative, preferably 5 to 30 mole %, more preferably 5 to 20 mole %, of terephthalic acid or its ester-forming derivative, and preferably 3 to 30 mole %, more preferably 3 to 14 mole %, of 2,6-naphthalenedicarboxylic acid or its ester-forming derivative. The glycol component of the polyester resin contain, based on the total amount of the glycol component, preferably 80 to 95 mole %, more preferably 85 to 93 mole %, of ethylene glycol, and preferably 5 to 20 mole %, more preferably 7 to 15 mole %, of diethylene glycol.

In preparing the polyester resin (B) of the polyester resin composition to be used for a reduced pressure blood-collecting tube, it is utterly suitable to use, based on the total amount of the dicarboxylic acid component, 85 to 97 mole % of a combination of isophthalic acid or its ester-forming derivative with terephthalic acid or its ester-forming derivative and 3 to 15 mole % of 2,6-naphthalenedicarboxylic acid or its ester-forming derivative.

In the polyester resin (B) for use in the present invention, it is possible to use any of the compounds exemplified above as the polycondensation component of the polyethylene terephthalate polymer (A) insofar as the dicarboxylic acid component and glycol component are within the specified ranges of the invention.

The dicarboxylic acid component may be partly replaced by a small amount of at least one of hexahydro-terephthalic acid, hexahydroisophthalic acid, hydroxybenzoic acid, diphenyldicarboxylic acid, diphenyl ether dicarboxylic acid, diphenyl sulfone dicarboxylic acid, phenoxy ethanedicarboxylic acid, 3,5-dicarboxybenzenesulfonic acid, oxalic acid, succinic acid, glutaric acid, sebacic acid, and their ester-forming derivatives.

The ethylene glycol may be partly replaced by a small amount of at least one of cyclohexanedimethanol, propylene glycol, trimethylene glycol, tetramethylene glycol, pentamethylene glycol, hexamethylene glycol, neopentyl glycol, and polyalkylene glycol such as polyethylene glycol, polytetramethylene glycol and polypropylene glycol.

Polyfunctional compounds are also useful as other polycondensation component, e.g. trimellitic acid, pyromellitic acid and the like as the acid component.

The amount of the polyfunctional compound component to be used should be limited to the range wherein the polyester resin (B) can substantially retain the linear form.

The polyester resin (B) can be prepared, for example, from isophthalic acid or its ester-forming derivative, terephthalic acid or its ester-forming derivative, 2,6-naphthalenedicarboxylic acid or its ester-forming derivative, ethylene glycol and diethylene glycol by conducting, in the presence of a catalyst, an ester exchange reaction or an esterification reaction and then a polycondensation reaction under reduced pressure.

The intrinsic viscosity (IV) of the polyester resin (B) for use in the present invention is suitably adjusted to a range so as to attain good mixing with the polyethylene terephthalate polymer (A) in melt molding and the required mechanical properties of the molded product. Usually the IV of the resin (B) is in the range of 0.4 to 1.0 dl/g, preferably 0.5 to 0.85 dl/g.

The reaction catalysts and reaction stabilizers exemplified hereinbefore for use in preparing the polyethylene terephthalate polymer (A) can be used in said ester exchange reaction or said esterification reaction and polycondensation reaction.

Optionally the polyester resin (B) for use in the present invention may be heat-treated to increase the degree of polycondensation and to reduce the acetaldehyde content. It is possible to heat-treat the composition comprising the polyethylene terephthalate polymer (A) and the resin (B).

The polyester resin (B) for use in the invention may contain heat stabilizers, thermal-oxidative stabilizers, antistatic agents, weathering stabilizers, lubricants, pigments, dyes, pigment dispersants, and the like within the range not adversely affecting the objects of the invention.

According to the present invention, the polyester resin composition comprises 90 to 10% by weight of the polyethylene terephthalate polymer (A) and 10 to 90% by weight of the polyester resin (B), preferably 90 to 40% by weight of the polyethylene terephthalate polymer (A) and 10 to 60% by weight of the polyester resin (B).

Less than 10% by weight of the polyester resin (B) used does not impart a satisfactory gas barrier property to the obtained molded product, whereas more than 90% by weight of the polyester resin (B) used lowers the heat resistance and impact strength of the obtained molded product.

The polyester resin composition of the present invention is prepared by conventional methods capable of uniformly mixing the polyethylene terephthalate polymer (A) and the polyester resin (B), such as methods wherein the resins (A)

and (B) are mixed using a double-conical blender, ribbon blender, and the like. Optionally the resins blended by these methods may be melt-kneaded by a single-screw extruder, a double-screw extruder, a vented extruder or the like and granulated.

The polyester resin composition of the present invention may contain optional component in addition to said essential component, i.e. the polyethylene terephthalate polymer (A) and the polyester resin (B), within the range not adversely affecting the objects of the invention. Useful optional component include, for example, thermoplastic resins such as polyamide resins and polyolefin resins, heat stabilizers, thermal-oxidative stabilizers, antistatic agents, weathering stabilizers, lubricants, pigments, dyes, salts of transition metals such as cobalt, pigment dispersants, and the like.

The polyester resin composition of the invention may be molded into stretched or unstretched films, sheets, trays, stretched hollow containers, direct blow-molded containers, other packaging materials, reduced pressure blood-collecting bottom-ended tubes and the like.

The polyester resin composition of the invention has excellent gas barrier property owing to blending of the polyester resin (B) having high gas barrier property. A sheet molded from the polyester resin composition of the invention has an oxygen permeability coefficient of 3.0 or less cc·mm/m$^2$·day·atm, namely a sufficient gas barrier property. A preferred oxygen permeability coefficient of the sheet is 2.4 cc·mm/m$^2$·day·atm.

A bottom-ended tube formed from the polyester resin composition of the invention, when used as a reduced pressure blood-collecting tube, can make the most of its gas barrier property, transparency, impact strength and the like, and is therefore useful. The reduced pressure blood-collecting tube is bottom-ended and has a sealing plug for closing the open end. Stated more specifically, the tube consists of (i) a bottom-ended hollow body which is open at one end and closed in the other end, and (ii) a sealing plug for closing the open end, wherein the plug can be pierced with a sharp-pointed needle of a blood-collecting instrument and the inside of the tube is held at a reduced pressure. The bottom-ended tube has an outside diameter of 10 to 20 mm, a length of 60 to 170 mm and a wall thickness of 1 to 2 mm.

The molded product, i.e. the bottom-ended tube of the polyester resin composition of the invention, can be produced by molding methods such as injection molding, extrusion molding, biaxial stretching molding, vacuum forming, compression molding, pipe extrusion molding, co-injection molding and the like.

The open end of the tube is closed with a sealing plug made of natural rubber, synthetic rubber, thermoplastic elastomer or the like, and the internal pressure of the tube is reduced by conventional methods, whereby a reduced pressure blood-collecting tube is formed. The inner wall of the bottom-ended tube may be subjected to a hydrophilic treatment, e.g. to become coated with a hydrophilic substance, or to other treatments, e.g. to deposit thereon a blood coagulation inhibitor or a blood coagulation accelerator.

The thus obtained reduced pressure blood-collecting bottom-ended tube can be used in clinical tests such as biochemical test, serologic test, hematological test or blood sugar test.

Two properties shown herein were evaluated by the following methods.
(1) Intrinsic viscosity (dl/g)
Measured using a solvent mixture of phenol and 1,1,2,2-tetrachloroethane (weight ratio of 3:2) at a temperature of 30° C.

(2) Oxygen permeability coefficient (cc·mm/m$^2$·day·atm)
Measured with an apparatus for measuring the oxygen permeability rate (trade name OX-TRAN 100 model manufactured by Mocon Co., Ltd.) at a temperature of 25° C. and a relative humidity of 50%.

The present invention will be described below in more detail with respect to the following Examples and Comparative examples. However, the present invention is not limited at all to the Examples.

The polyethylene terephthalate polymer (A) and the polyester resin (B) used in the Examples and Comparative Examples are as follows.
(i) Polyethylene terephthalate polymer (A)
Used as the polymer (A) was a polyethylene terephthalate resin manufactured by Nippon Unipet Co., Ltd. (trade name "RT 543") and having an intrinsic viscosity (IV) of 0.75 dl/g. The polymer (hereinafter referred to as "polymer (a-1)") had 97 mole % of ethylene terephthalate units and 3 mole % of diethylene terephthalate units. The polymer (a-1) was molded into an unstretched sheet having a thickness of 0.1 mm by a press sheet-molding machine (manufactured by Shinto Co., Ltd.). The sheet had an oxygen permeability coefficient of 4.2 cc·mm/m$^2$·day·atm.
(ii) Polyester resin (B)
An ester exchange reaction was conducted in an autoclave using dimethyl isophthalate, dimethyl terephthalate, dimethyl 2,6-naphthalene dicarboxylate, ethylene glycol and diethylene glycol in the presence of magnesium acetate, giving an initial condensate. The initial condensate was subjected to polycondensation in the presence of antimony trioxide, giving a polyester resin (b-1). In this way, polyester resins (b-2) to (b-7) were produced.

Table 1 below shows the compositions of the dicarboxylic acid component and the glycol component in each polyester resin. The compositions were determined by $^1$H-NMR. The polyester resins (b-1) to (b-7) were molded into 0.1 mm-thick unstretched sheets by a press sheet-molding machine (manufactured by Shinto Co., Ltd.). Table 1 also shows the oxygen permeability coefficient of the obtained sheets.

TABLE 1

| Polyester resin | Dicarboxylic acid component (mole %) | | | Glycol component (mole %) | | Oxygen permeability coefficient (cc · mm/m$^2$ · day · atm) | Intrinsic viscosity (dl/g) |
|---|---|---|---|---|---|---|---|
| | DMI | DMT | DMN | EG | DEG | | |
| (b-1) | 92 | 5 | 3 | 98 | 2 | 1.2 | 0.81 |
| (b-2) | 73 | 8 | 19 | 97.5 | 2.5 | 1.8 | 0.82 |
| (b-3) | 84 | 11 | 5 | 96 | 4 | 1.4 | 0.80 |
| (b-4) | 85 | 10 | 5 | 90 | 10 | 1.2 | 0.81 |
| (b-5) | 85 | 10 | 5 | 85 | 15 | 1.2 | 0.82 |
| (b-6) | 85 | 10 | 5 | 75 | 25 | 1.5 | 0.81 |
| (b-7) | 85 | 10 | 5 | 70 | 30 | 1.5 | 0.81 |

In Table 1, DMI is short for dimethyl isophthalate, DMT for dimehtyl terephthalate, DMN for dimethyl 2,6-naphthalene dicarboxylate, EG for ethylene glycol and DEG for diethylene glycol.

EXAMPLES 1–4 and Comparative Examples 1–4

The polyethylene terephthalate polymer (a-1) and each of the polyester resins (b-1) to (b-7) were dry-blended in the proportion shown below in Table 2, giving a polyester resin composition according to the present invention or a comparative polyester resin composition. The obtained compositions were molded into 0.1 mm-thick unstretched sheets by a press sheet-molding machine (manufactured by Shinto Co., Ltd.). The obtained sheets had the oxygen permeability coefficient shown in Table 2.

TABLE 2

| | Polyethylene terephthalate polymer | | Polyester resin | | Oxygen permeability coefficient (cc · mm/m² · day · atm) |
|---|---|---|---|---|---|
| | Type | Wt. part | Type | Wt. part | |
| Example 1 | (a-1) | 70 | (b-3) | 30 | 2.4 |
| Example 2 | (a-1) | 60 | (b-4) | 40 | 1.7 |
| Example 3 | (a-1) | 60 | (b-5) | 40 | 1.9 |
| Example 4 | (a-1) | 60 | (b-6) | 40 | 1.5 |
| Comp. Ex. 1 | (a-1) | 100 | Not used | — | 4.2 |
| Comp. Ex. 2 | (a-1) | 60 | (b-1) | 40 | 1.9 |
| Comp. Ex. 3 | (a-1) | 60 | (b-2) | 40 | 2.0 |
| Comp. Ex. 4 | (a-1) | 60 | (b-7) | 40 | 1.5 |

EXAMPLES 5–8 and Comparative Examples 5–8

Each of the polyester resin compositions prepared in Examples 1–4 and Comparative Examples 1–4 was molded into a bottom-ended tube (vol.10 cc) having an outside diameter of 13 mm, a length of 150 mm and a wall thickness of 1.5 mm using an injection molding machine (manufactured by Toshiba Machine Co., Ltd.). The opening at one end of the tube was closed with a plug made of synthetic rubber. The pressure inside the tube was so reduced as to adjust the initial water absorption to 6 cc, producing a reduced pressure blood-collecting tube for the present invention or for a comparative purpose.

Each of the reduced pressure blood-collecting tubes obtained above was subjected to performance tests in respect of the change in water absorption with time, drop impact strength and heat resistance by the following methods.

(1) Change in Water Absorption With Time

The reduced pressure blood-collecting tube with an initial water absorption of 6 cc was held at room temperature. The change in water absorption after specific lapse of time was assessed.

(2) Drop Impact Strength

The reduced pressure blood-collecting tube was cooled to 0° C. and dropped onto the surface of concrete substrate from a height of 2 m to check the cracking. The test was conducted to evaluate 50 samples of each tube. The drop impact strength was expressed in the number of broken tubes.

(3) Heat resistance

After each tube was heated to about 60° C., the inside of the tube was brought to a reduced pressure of 1 torr or less and was retained in this state for 1 hour. Then the tube was visually inspected to evaluate the change of its shape according to the following criteria: A, no change (excellent in heat resistance); B, slightly changed (a little low in heat resistance); and C, greatly changed (low in heat resistance).

The results of the tests are shown in Table 3.

TABLE 3

| | Water absorption (cc) | | | Drop impact strength (number of broken tubes) | Heat resistance |
|---|---|---|---|---|---|
| | Initial | 3 months later | 6 months later | | |
| Example 5 | 6.0 | 5.9 | 5.7 | 5 | A |
| Example 6 | 6.0 | 5.9 | 5.8 | 3 | A |
| Example 7 | 6.0 | 5.9 | 5.8 | 3 | A |
| Example 8 | 6.0 | 5.9 | 5.7 | 2 | B |
| Comp. Ex. 5 | 6.0 | 5.4 | 4.9 | 5 | A |
| Comp. Ex. 6 | 6.0 | 5.9 | 5.8 | 12 | A |
| Comp. Ex. 7 | 6.0 | 5.7 | 5.4 | 10 | A |
| Comp. Ex. 8 | 6.0 | 5.8 | 5.6 | 2 | C |

When the polyester resin composition of the present invention is used in forming molded products, the obtained molded products are excellent in transparency, gas barrier property, ultraviolet-screening property, impact strength, especially drop impact strength, and heat resistance.

Consequently the obtained molded products are utterly suitable as reduced pressure blood-collecting tubes. That is, the blood-collecting tube of the invention is scarcely variable in the amount of collected blood with time because of its high gas barrier property and is outstanding also in ultraviolet-screening property, transparency, drop impact strength and heat resistance.

What is claimed is:

1. A polyester resin composition comprising:
   (A) 10 to 90% by weight of a polyethylene terephthalate polymer having 100 to 75 mole % of ethylene terephthalate units; and
   (B) 90 to 10% by weight of a polyester resin, the polyester resin being prepared by polycondensation of the dicarboxylic acid component and glycol component, the dicarboxylic acid component comprising, based on the total amount of the dicarboxylic acid component, 50 to 92 mole % of isophthalic acid or its ester-forming derivative, 5 to 47 mole % of terephthalic acid or its ester-forming derivative and 3 to 45 mole % of 2,6-naphthalenedicarboxylic acid or its ester-forming derivative, and the glycol component comprising, based on the total amount of the glycol component, 75 to 96.5 mole % of ethylene glycol and 3.5 to 25 mole % of diethylene glycol,
   the polyester resin composition, when molded into a sheet, having an oxygen permeability coefficient of 3.0 cc·mm/m²·day·atm or less.

2. The polyester resin composition according to claim 1, wherein the polyethylene terephthalate polymer (A) has an intrinsic viscosity (IV) of 0.4 to 1.2 dl/g.

3. The polyester resin composition according to claim 1, wherein the polyester resin (B) has an intrinsic viscosity (IV) of 0.4 to 1.0 dl/g.

4. The polyester resin composition according to claim 1, wherein the compositions, when molded into a sheet, has an oxygen permeability coefficient of 2.4 cc·mm/m²·day·atm or less.

5. The polyester resin composition according to claim 1, wherein the dicarboxylic acid component in the polyester (B) comprises, based on the total amount of the dicarboxylic acid component, 70 to 90 mole % of isophthalic acid or its ester-forming derivative, 5 to 30 mole % of terephthalic acid or its ester-forming derivative, and 3 to 30 mole % of 2,6-naphthalenedicarboxylic acid or its ester-forming derivative.

6. The polyester resin composition according to claim 1, wherein the glycol component in the polyester rein (B) comprises, based on the total amount of the glycol component, 80 to 95 mole % of ethylene glycol, and 5 to 20 mole % of diethylene glycol.

7. The polyester resin composition according to claim 1, wherein the polyester resin (B), when molded into a sheet, has an oxygen permeability coefficient of 3.0 cc·mm/ m$^2$·day·atm or less.

8. The polyester resin composition according to claim 1, wherein the composition comprises 90 to 40% by weight of the polyethylene terephthalate polymer (A) and 10 to 60% by weight of the polyester resin (B).

9. A molded product formed from the polyester resin composition of claim 1.

10. A reduced pressure blood-collecting tube having a bottom at one end thereof and a plug for closing the opening at the other end thereof, said tube being molded from the polyester resin composition of claim 1.

11. The reduced pressure blood-collecting tube according to claim 10, wherein the polyester resin (B) of the polyester resin composition constituting the tube has the dicarboxylic acid component comprising, based on the total amount of the dicarboxylic acid component, 85 to 97 mole % of a combination of isophthalic acid or its ester-forming derivative and terephthalic acid or its ester-forming derivative, and 3 to 15 mole % of 2,6-naphthalenedicarboxylic acid or its ester-forming derivative.

* * * * *